(12) United States Patent
Golias

(10) Patent No.: US 12,339,248 B2
(45) Date of Patent: Jun. 24, 2025

(54) WASH FOR ELECTROPHORESIS

(71) Applicant: HELENA LABORATORIES CORPORATION, Beaumont, TX (US)

(72) Inventor: Tipton L Golias, Beaumont, TX (US)

(73) Assignee: HELENA LABORATORIES CORPORATION, Beaumont, TX (US)

( * ) Notice: Subject to any disclaimer, the term of this patent is extended or adjusted under 35 U.S.C. 154(b) by 352 days.

(21) Appl. No.: 18/017,427

(22) PCT Filed: May 11, 2021

(86) PCT No.: PCT/US2021/031791
§ 371 (c)(1),
(2) Date: Jan. 23, 2023

(87) PCT Pub. No.: WO2022/031337
PCT Pub. Date: Feb. 10, 2022

(65) Prior Publication Data
US 2023/0273152 A1    Aug. 31, 2023

Related U.S. Application Data

(60) Provisional application No. 63/061,277, filed on Aug. 5, 2020.

(51) Int. Cl.
*G01N 27/447* (2006.01)
*G01N 33/561* (2006.01)

(52) U.S. Cl.
CPC ..... *G01N 27/44704* (2013.01); *G01N 33/561* (2013.01)

(58) Field of Classification Search
CPC ...................... G01N 27/44704; G01N 33/561
See application file for complete search history.

(56) References Cited

U.S. PATENT DOCUMENTS

2008/0207481 A1    8/2008   Meine et al.

FOREIGN PATENT DOCUMENTS

EP          0454928        11/1991
WO      2017/157985        9/2017

OTHER PUBLICATIONS

Labome. Detergents: Triton X-100, Tween-20, and More. Mater Methods, 2013; 3: 163, https://www.labome.com/method/Detergents-Triton-X-100-Tween-20-and-More.html (Year: 2013).*

(Continued)

*Primary Examiner* — Luan V Van
*Assistant Examiner* — Randall Lee Gamble, Jr.
(74) *Attorney, Agent, or Firm* — Jerold I. Schneider; SCHNEIDER IP LAW

(57) ABSTRACT

A wash solution for removal of unbound proteins, unreacted antisera, and excess stain from an electrophoresis gel plate and a method of using the wash solution. The wash solution contains one or more of Hexamethylindanopyran, Tetramethyl acetyloctahydronaphthalenes, Hexyl cinnamal, Butylphenyl methylpropional, d-Limonene and Linalool. Alternatively, the wash solution react with lipids and fats in the unbound proteins and/or unreacted antisera, and/or causes pores in the gel to expand yielding a more efficient removal of unbound protein and unbound antisera, and/or contains protease enzymes that digest proteins and an amylase enzyme to hydrolyze starches and sugars.

14 Claims, 2 Drawing Sheets

(56) References Cited

OTHER PUBLICATIONS

Link. Immunoglobulin Class and Light Chain Type of Oligoclonal Bands in CSF in Multiple Sclerosis Determined by Agarose Gel Electrophoresis and Immunofixation. Annals of Neurology, 1979; 6(2), 107-110 (Year: 1979).*

Quinn et al, Moderate statin treatment reduces prebeta-1 high-density lipoprotein levels in dyslipidemic patients, Journal of Clinical Lipidology, Elsevier, New York, N.Y. (US) vol. 11, No. 4, May 4, 2017, pp. 908-914.

Goodland et al, A comparison of cellulose acetate immunofixation with polyacrylamide gel electrophoresis for the detection of oligoclonal bands in unconcentrated cerebrospinal fluid, Journal of Clinical Pathology, vol. 36, No. 11, Nov. 1, 1983, pp. 1309-1311.

Gyorgy Csako Immunofixation electrophoresis for identification of proteins and specific antibodies (In Protein Electrophoresis, 2012, New York, Heidelberg Press) pp. 147-171—Humana Press.

International Search Report for PCT/US2021/031791 dated Sep. 30, 2021.

Written Opinion of ISA for PCT/US2021/031791 dated Sep. 30, 2021.

* cited by examiner

Clear Wash Solution

WASH FOR ELECTROPHORESIS

BACKGROUND OF THE INVENTION

The present invention relates to electrophoresis procedures in general and, in particular, to a method for enhancing the clarity of the results of an immunofixation electrophoresis procedure.

IMMUNOFIXATION ELECTROPHORESIS

Immunofixation electrophoresis, frequently referred to as IFE, is well-known as a two-stage procedure for detecting the presence of certain proteins in human serum, urine or cerebral spinal fluid. The procedure involves, as a first step, protein fraction resolution by electrophoresis. As a second step, the soluble antigen in the protein is allowed to react with an externally applied antibody (antiserum). The resultant antigen-antibody complexes will precipitate, at a rate dependent upon the proportion of the reactants, temperature, salt concentration and pH. The antigen-antibody complexes are then visualized by staining.

Typically, a specimen from a single patient is diluted and then placed in multiple sample or application areas, frequently referred to as zones or lanes, on a single electrophoretic gel plate. The gel plate may be an agarose gel, a polyacrylamide gel, or other suitable gel. The purpose of utilizing multiple sample areas for a single patient, is to enable detection, separately, of total serum protein, various proteins such as the immunoglobin heavy chains IgG, IgM, IgA and light chains Kappa and Lambda, or other proteins whose presence or absence may be of importance in medical diagnosis. As known in the prior art, various antisera (i.e., fluid containing the antibody) such as IgG, IgM, etc., are deposited on the appropriate lanes and permitted to react with the antigen in the sample. The term "incubation" refers to the time interval during which the antisera and antibody are in contact such that a reaction may occur. Improvements in the IFE procedure and equipment have progressed such that a single gel plate may accommodate not only multiple sample areas for a single patient, but also may accommodate multiple patients. Thus, if six zones or lanes are utilized for a single patient, and if a single gel plate accommodates nine patients, then there may be 54 lanes on the single gel plate.

After the electrophoretic separation step, the entire reaction zones or lanes must be covered with the appropriate antiserum since the antisera-antigen reaction or resolution, frequently referred to as the protein fraction resolution, may occur virtually at any position along the respective reaction zones. If the entire zone is not covered, depending on the location of the antigen in the patient sample, an antibody-antigen reaction may not occur. Therefore, covering the entire zone is important for qualitative purposes. Furthermore, there must be sufficient antiserum deposited such that all the antigen in the patient sample will react, otherwise the quantitative aspect of the test will be compromised. Therefore, it is conventional to apply excess amounts of antiserum.

After the incubation period, the relative percentage of the protein in each fraction or lane is obtained. All the unreacted antisera and all unbound proteins should be removed prior to staining and visualization analysis otherwise, unreacted antisera and unbound proteins will increase the noise to true signal ratio leading to a reduction in diagnostic efficacy. To explain this further, consider, merely for illustrative purposes one lane such as the IgG lane, i.e., the lane where the antisera for IgG is to be deposited. There must be excess antisera deposited to provide a reaction with all the IgG present in the sample. All the IgG in the patient sample should be bound to antisera for accurate results. After the incubation period, the excess antisera must be removed to eliminate noise. However, the patient sample included numerous proteins not just IgG and all the proteins are present in each lane. The proteins that did not bind to the antisera, referred to as the unbound proteins, must also be removed. In this example, all the unreacted proteins in the IgG lane must be removed.

Historically, the removal of unbound proteins and excess or unreacted antisera was removed by a multistep washing and blotting procedure. As a non-limiting example, a typical procedure comprises a series of alternating blotting and rehydrating steps. The blotting steps remove excess antisera and unbound proteins, collectively referred to as fluid, from the gel plate and the blotting steps are carried out at elevated temperatures of approximately 50° C. (approximately 122° F.). Between each blotting step, i.e., after each blotting step except the last blotting step, the unreacted proteins and excess antisera in the gel are rehydrated, such as with TBS, at room temperature of approximately 22° C. (72° F.). The blotting and rehydrating steps may be repeated three times followed by a final blotting step. TBS refers to tris-buffered saline, a solution of approximately 40% Tris-HCl, 21% Tris Base, and 39% NaCl with a pH of 7.5. Tris is tris(hydroxymethyl)aminomethane.

After the removal of unbound proteins and unreacted antisera, a stain, such as but not limited to an acid violet stain is applied to visualize the result of the antibody-antigen reaction. The excess stain is then removed by a destaining process.

Conventional wash (rehydration) at room temperature and drying (blotting) at elevated temperatures have been known for at least the last 75 years.

SUMMARY

The present invention relates to an improvement in the removal of unbound proteins, unreacted antisera, and excess stain by an improved wash solution.

DETAILED DESCRIPTION

Figure 1:
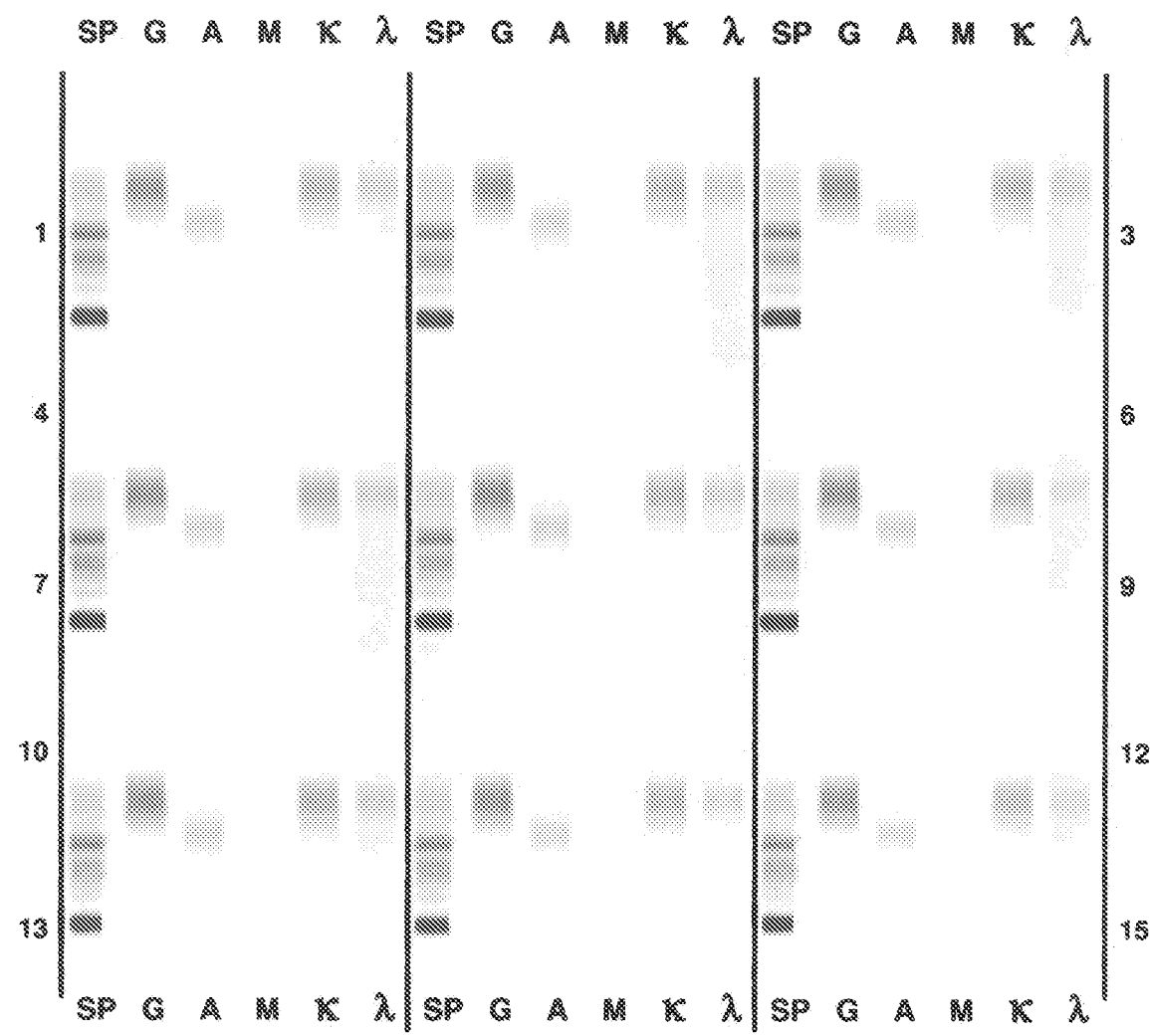
FIG. 1 illustrates a gel plate used in IFE with conventional removal of unbound proteins and unreacted antisera, using a conventional wash such as TBS.

FIG. 1 illustrates a conventional gel plate after IFE, staining, and conventional removal of unbound proteins and unreacted antisera. The gel plate in FIG. 1 accommodates nine patient samples in a 3×3 array. The first horizontal row illustrates the results for patients 1, 2, and 3, the second horizontal row illustrates the IFE results for patients 4, 5 and 6, and the third horizontal row illustrates the IFE results for patients 7, 8 and 9.

For each patient there are six vertical columns, referred to as lanes or zones, identified as SP (indicating total serum protein), G, A, M, κ (Kappa) and λ (Lambda)

The nine patient samples on the IFE gel plate for FIG. 1 were processed using a conventional "wash" and "dry" procedure with conventional blotting and rehydration times and temperatures as describe above with the rehydration occurring at room temperature, i.e., approximately 22° C. (72° F.).

Figure 2:
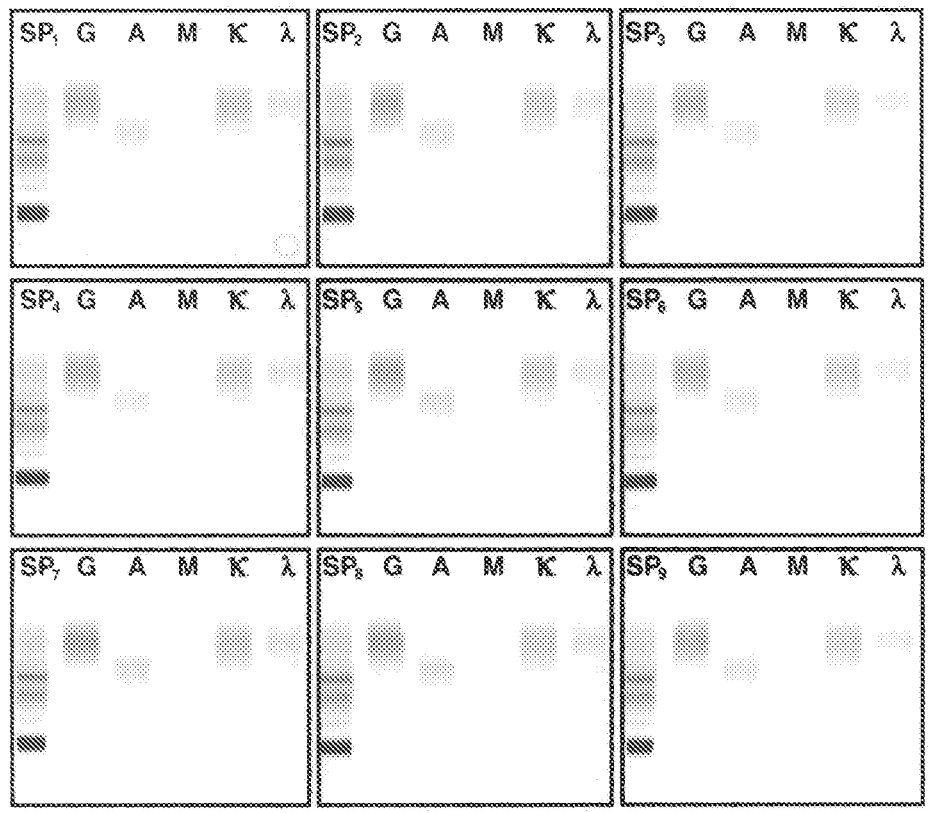
FIG. 2 illustrates a gel plate used in IFE with removal of unbound proteins and unreacted antisera using the improved wash solution.

FIG. 2 illustrates a conventional gel plate after IFE, staining, and removal of unbound proteins and unreacted antisera using the improved wash solution. The gel plate in FIG. 2 accommodates nine patient samples in a 3×3 array. The first horizontal row illustrates the results for patients 1, 2, and 3, the second horizontal row illustrates the IFE results for patients 4, 5 and 6, and the third horizontal row illustrates the IFE results for patients 7, 8 and 9.

For each patient there are six vertical columns, referred to as lanes or zones, identified as SP (indicating total serum protein), G, A, M, κ (Kappa) and λ (Lambda)

The nine patient samples on the IFE gel plate for FIG. 2 were processed using the same patient samples or specimens and the same "wash" and "dry" procedure with conventional blotting and rehydration times and temperatures as describe above with the rehydration occurring at room temperature, i.e., approximately 22° C. (72° F.) but using the improved wash.

A comparison of the actual gel plates indicates greater clarity in the lanes of the of the FIG. 2 gel plate, less "background" and thus more reliable results. While the Figures cannot provide the total degree of clarity as would be apparent on inspection of the actual gel plates, the Figures indicate, for example in the Lambda (λ) lane, that there has been a substantial decrease in "background", i.e., a substantial decrease in unbound proteins and unreacted antisera.

It is believed, from a theoretical perspective, that the wash solution may react with lipids and fats in the unbound proteins and/or unreacted antisera to aid in removing unbound proteins and/or unreacted antisera from the agarose plate. Alternatively, or additionally, it is believed from a theoretical perspective, that the wash solution may cause the agarose pores in the gel to expand yielding a more efficient removal of unbound protein and unbound antisera.

The enhanced removal of unbound proteins and/or unreacted antisera reduces unwanted background staining.

A suitable wash solution includes:
(1) Water; and
(2) One or more of:
   a. Hexamethylindanopyran—$C_{18}H_{26}O$ also known as Galaxolide;
   b. Tetramethyl acetyloctahydronaphthalenes—$C_{16}H_{26}O$;
   c. Hexyl cinnamal—$C_{15}H_{20}O$;
   d. Butylphenyl methylpropional—also known as Lilial—$C_{14}H_{20}O$,
   e. d-Limonene—$C_{10}H_{16}$; and
   f. Linalool—$C_{10}H_{18}O$.

It is believed, subject to further investigation, that one or more of the ingredients 2(a) through 2(f) contains protease enzymes that digest proteins (including lipoproteins) and an amylase enzyme to hydrolyze starches and sugars. These enzymes seem to aid in clearing the background from the gel.

The temperature for the blotting step is in the range of 40° C. to 60° C., preferably 45° C. to 55° C. and most preferably approximately 50° C. The temperature for the rehydration step is in the range of 12° C. to 32° C., preferably 17° C. to 27° C. and most preferably approximately 22° C.

What is claimed is:

1. An improved wash solution for removing unbound proteins and unreacted antisera from a gel plate in an immunofixation (IFE) system, the wash solution including at least one of the components (a) through (f):

a) Hexamethylindanopyran—$C_{18}H_{26}O$ also known as 1,3,4,6,7,8-hexahydro-4,6,6,7,8,8,-hexamethyl-cyclopenta[g]benzopyran or HHCB;
   b) Tetramethyl acetyloctahydronaphthalenes—$C_{16}H_{26}O$;
   c) Hexyl cinnamal—$C_{15}H_{20}O$;
   d) Butylphenyl methylpropional—$C_{14}H_{20}O$;
   e) d-Limonene—$C_{10}H_{16}$; and
   f) 3,7-Dimethyl-3-hydroxy-1,6-octadiene—$C_{10}H_{18}O$.

2. The improved wash solution according to claim 1 including at least two of the components (a) through (f).

3. A method of removal of unbound proteins and unreacted antisera from a gel plate in an IFE system wherein patient samples are applied to the gel plate in a plurality of lanes, different antisera are applied to at least two of the plurality of lanes to cause an antibody-antisera reaction in each lane, the method including a step of washing the unbound proteins and the unreacted antisera from the gel plate, the improvement of washing the unbound proteins and the unreacted antisera from the gel plate using the wash solution of claim 1.

4. A method of removing unbound proteins and unreacted antisera from an agarose gel plate in an immunofixation (IFE) system wherein patient samples are applied to the agarose gel plate in a plurality of lanes, different antisera are applied to at least two of the plurality of lanes to cause an antibody-antisera reaction in each lane, the improvement of washing the unbound proteins and the unreacted antisera from the agarose gel plate using a wash solution of claim 1 that provides at least one of the following steps:
   a. reacting with lipids in the unbound proteins to aid in removing the unbound proteins from the agarose gel plate;
   b. reacting with the lipids in the unreacted antisera to aid in removing the lipids from the agarose gel plate;
   c. reacting with fats in the unbound proteins to aid in removing the unbound proteins from the agarose gel plate;
   d. reacting with fats in the unreacted antisera to aid in removing the unreacted antisera from the agarose gel plate;
   e. causing pores in the agarose gel plate to expand;
   f. digesting the unreacted proteins on the agarose gel plate;
   g. hydrolyzing starches on the agarose gel plate;
   h. hydrolyzing sugars on the agarose gel plate.

5. The method according to claim 3 wherein the step of washing is carried out at a temperature in a range of 12° C. to 32° C.

6. The method according to claim 3 wherein the step of washing is carried out at a temperature in a range of 17° C. to 27° C.

7. The method according to claim 3 wherein the step of washing is carried out at a temperature of approximately 22° C.

8. The method according to claim 4 wherein the step of washing is carried out at a temperature in the range of 12° C. to 32° C.

9. The method according to claim 4 wherein the step of washing is carried out at a temperature in the range of 17° C. to 27° C.

10. The method according to claim 4 wherein the step of washing is carried out at a temperature of approximately 22° C.

11. The improved wash solution according to claim 1 and including three of the components (a) through (f).

12. The improved wash solution according to claim 1 and including four of the components (a) through (f).

13. The improved wash solution according to claim 1 and including five of the components (a) through (f).

14. The improved wash solution according to claim 1 and including all of the components (a) through (f).

* * * * *